(12) United States Patent
Froggatt et al.

(10) Patent No.: US 10,245,115 B2
(45) Date of Patent: Apr. 2, 2019

(54) FIBER OPTIC SENSING OF TOOL STRAIN OR TOOL ANGLE

(71) Applicant: INTUITIVE SURGICAL OPERATIONS, INC., Sunnyvale, CA (US)

(72) Inventors: Mark Froggatt, Blacksburg, VA (US); Eric Sanborn, Blacksburg, VA (US); Alexander K. Sang, Blacksburg, VA (US); Matthew S. Wolfe, Blacksburg, VA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 15/670,310

(22) Filed: Aug. 7, 2017

(65) Prior Publication Data

US 2018/0064500 A1  Mar. 8, 2018

Related U.S. Application Data

(60) Provisional application No. 62/383,914, filed on Sep. 6, 2016.

(51) Int. Cl.
*G01B 11/16* (2006.01)
*A61B 34/00* (2016.01)
(Continued)

(52) U.S. Cl.
CPC .............. *A61B 34/76* (2016.02); *A61B 34/70* (2016.02); *A61B 90/06* (2016.02); *G01L 1/242* (2013.01);
(Continued)

(58) Field of Classification Search
CPC ....... G01L 1/246; G01L 1/242; G01L 11/025; G01L 1/00; G01L 1/26; G01L 11/02;
(Continued)

(56) References Cited

U.S. PATENT DOCUMENTS 5,807,265 A  9/1998  Itoigawa et al.
7,050,662 B2  5/2006  Behrmann et al.
(Continued)

OTHER PUBLICATIONS

Gillooly A., "Fiber Sensing: Medical Fiber-Optic Sensors Offer Haptics, 3D Shape Sensing, and Pressure Sensing," pp. 43-46, [online], [retrieved on Aug. 23, 2016]. Retrieved from the Internet: URL: http://digital.laserfocusworld.com/laserfocusworld/201608/Print_submit.action?articleTitle=&articlePrintMode=false&start=45&end=49&prettyPrint=false&Im=1%E2%80%A6.
(Continued)

*Primary Examiner* — Michael P Stafira
(74) *Attorney, Agent, or Firm* — Nixon & Vanderhye P.C.

(57) ABSTRACT

A hinged tool includes a first member; a second member pivotally connected to the first member at a pivot; and an optical fiber. The optical fiber is fixed to the first member at a load application region and fixed to at least one of the pivot and the second member at a location such that the optical fiber bends when the first member and the second member are pivoted with respect to one another. A method of using a hinged tool includes measuring fiber strain in an optical fiber fixed to the hinged tool, and determining at least one of tool strain applied to the hinged tool and a degree of pivoting of the hinged tool using the fiber strain.

20 Claims, 11 Drawing Sheets

(51) Int. Cl.
*G02B 6/02* (2006.01)
*G01L 1/24* (2006.01)
*A61B 90/00* (2016.01)

(52) U.S. Cl.
CPC .... *G02B 6/02042* (2013.01); *A61B 2090/064* (2016.02); *A61B 2090/067* (2016.02); *G01B 11/16* (2013.01)

(58) Field of Classification Search
CPC ... G01L 25/00; G01L 5/12; G01L 9/04; G01L 5/0023; G01L 5/0052; G01L 5/166; G01L 1/005; G01L 1/12; G01L 1/22; G01L 1/2225; G01L 1/243; G01L 3/108; G01L 3/12; G01L 3/14; G01L 5/00; G01L 5/0009; G01L 5/0028; G01L 5/0038; G01L 5/0057; G01L 5/0076; G01L 5/04; G01L 5/107; G01L 5/133; G01L 5/16; G01L 5/167; G01L 9/0079; G01B 11/18; G01B 11/16; G01B 11/165; G01B 11/161; G01B 11/24; G01B 11/168; G01B 7/16; G01B 11/255; G01B 11/14; G01B 11/2441; G01B 11/26; G01B 2290/25; G01B 7/20; G01B 9/02002; G01B 9/02004; G01B 9/02044; G02B 6/00; G02B 6/02076; G02B 6/02042; G02B 6/34; G02B 6/022; G02B 6/10; G02B 6/2773; G02B 23/26; G02B 6/0208; G02B 6/124; G02B 2006/02157; G02B 2006/12097; G02B 2006/12104; G02B 2006/12111; G02B 2006/12138; G02B 2006/1215; G02B 23/2484; G02B 27/017; G02B 6/02085; G02B 6/02114; G02B 6/02123; G02B 6/02209; G02B 6/12004; G02B 6/12019; G02B 6/122; G02B 6/126; G02B 6/255; G02B 6/2551; G02B 6/2552; G02B 6/262; G02B 6/264; G02B 6/2726; G02B 6/2766; G02B 6/2786; G02B 6/2861; G02B 6/293; G02B 6/2938; G02B 6/32; G02B 6/3608; G02B 6/3612; G02B 6/3628; G02B 6/3636; G02B 6/3692; G02B 6/3846; G02B 6/4402; G02B 6/4415; G02B 6/4428; G02B 6/4432; G02B 6/4477; G02B 6/4486

See application file for complete search history.

(56) References Cited

U.S. PATENT DOCUMENTS

| | | | |
|---|---|---|---|
| 7,388,190 B2* | 6/2008 | Huang | G01B 11/18 250/227.14 |
| 7,720,322 B2 | 5/2010 | Prisco | |
| 7,781,724 B2 | 8/2010 | Childers et al. | |
| 8,460,236 B2 | 6/2013 | Roelle et al. | |
| 8,567,265 B2 | 10/2013 | Aeby et al. | |
| 8,672,837 B2 | 3/2014 | Roelle et al. | |
| 2003/0120286 A1* | 6/2003 | Burbank | A61B 5/415 606/142 |
| 2007/0049973 A1* | 3/2007 | Burbank | A61B 17/122 607/2 |
| 2011/0071543 A1* | 3/2011 | Prisco | A61B 17/0218 606/130 |
| 2013/0253489 A1* | 9/2013 | Nau, Jr. | A61B 18/22 606/16 |
| 2014/0005687 A1* | 1/2014 | Prisco | A61B 17/3421 606/130 |
| 2014/0121508 A1 | 5/2014 | Latimer et al. | |
| 2014/0238153 A1* | 8/2014 | Wood | G06F 3/011 73/862.627 |
| 2014/0336637 A1* | 11/2014 | Agrawal | A61B 18/1492 606/41 |
| 2015/0309563 A1* | 10/2015 | Connor | G06F 3/011 73/865.4 |
| 2016/0202755 A1* | 7/2016 | Connor | A61B 5/1126 73/865.4 |
| 2016/0338644 A1* | 11/2016 | Connor | G06F 3/014 |
| 2017/0354353 A1* | 12/2017 | Kim | A61B 5/6847 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

FIBER OPTIC SENSING OF TOOL STRAIN OR TOOL ANGLE

This application is claims the benefit of U.S. Provisional Application No. 62/383,914 filed Sep. 6, 2016, the entire contents of which is hereby incorporated by reference.

BACKGROUND

Various techniques for an optical fiber and applications thereof are known.

For example, the following patents all discuss aspects of detecting the shape of an optical fiber, or the application of such detection: U.S. Pat. Nos. 7,781,724, 7,720,322, 8,460,236, 8,672,837, 8,567,265, U.S. Patent Application Publication No. 2014/0121508, U.S. Pat. Nos. 7,050,662, and 5,807,265, all of which are hereby incorporated by reference in their entireties.

BRIEF SUMMARY

Precision information and/or tactile or other feedback (such as visual or aural) in medical instruments can be highly desirable. Precision information and/or tactile or other feedback may be even more desirable when operating a medical instrument remotely and interior to a patient's body. For example, tactile or other feedback may provide the user of the medical instrument (e.g., a doctor or clinician) a sensory experience similar to the instrument being in the user's hand even if it is operated remotely. Such tactile may increase the performance or confidence of the user. But medical instruments, including remotely operated instruments, may lack sufficient sensing capability to provide appropriate tactile feedback.

In addition, the ability to determine wear or breakage of a medical instrument may also be desirable, such as in gauging the useful life of the medical instrument and the safety of the patient.

One or more aspects of the present technology solves one or more problems of the prior art.

An aspect of the present technology includes a hinged tool comprising a first member; a second member pivotally connected to the first member at a pivot point; and an optical fiber. The optical fiber is fixed to the first member at a load application region. The optical fiber is fixed to at least one of the pivot and the second member (the pivot and/or the second member) at a location such that the optical fiber bends when the first member and the second member are pivoted with respect to one another.

In examples, (a) the optical fiber is fixed to the load application region along a predetermined length of the first member so that strain imparted to the first member along the predetermined length also imparts strain to the optical fiber along the predetermined length; (b) the load application region is a portion of the first member where strain is induced in the first member during use of the hinged tool; (c) the optical fiber is a multicore fiber comprising a plurality of optical cores configured for detecting strain; (d) the optical fiber is a single core fiber comprising a single core configured for detecting strain; (e) the load application region is between the pivot point and a distal end of the hinged tool; (f) the first member is not a monolithic body with any other structures (other than being fixedly bonded with the optical fiber) between the distal end and the pivot point; (g) the first member terminates at the distal end and is discrete from structures other than the optical fiber between the distal end and the pivot, such as between the distal end and the pivot point; (h) the first member and the second member together form a forceps; (i) the first member and the second member together form scissors; and/or (j) the optical fiber is fixed to the second member at the pivot, such as at the pivot point.

An aspect of the present technology includes a method of using a hinged tool, the method comprising: measuring fiber strain in an optical fiber fixed to the hinged tool; and determining at least one of tool strain applied to the tool and a degree of pivoting of the tool (i.e. the tool strain and/or the degree of pivoting) using the fiber strain.

In examples, (a) determining the at least one of the tool strain applied to the hinged tool and the degree of pivoting of the hinged tool using the fiber strain comprises: determining both the tool strain applied to the hinged tool and the degree of pivoting of the hinged tool; (b) determining the at least one of the tool strain applied to the hinged tool and the degree of pivoting of the hinged tool using the fiber strain comprises determining the tool strain applied to the hinged tool, and the method further comprises: correlating the fiber strain to a force applied to the hinged tool; (c) correlating the fiber strain to the force applied to the hinged tool comprises: correlating the fiber strain to a magnitude and distribution of force applied to the hinged tool; (d) the method further comprises adjusting the hinged tool based on the at least one of the tool strain applied to the hinged tool and the degree of pivoting of the hinged tool; (e) determining the at least one of the tool strain applied to the hinged tool and the degree of pivoting of the hinged tool using the fiber strain comprises: determining a distribution of the tool strain applied to the tool along a predetermined length of the tool; (f) the hinged tool comprises opposed jaws, and the method further comprises: determining a position where an object contacts the opposed jaws using the fiber strain, wherein the object is between the opposed jaws; (g) the hinged tool comprises opposed jaws, and the method further comprises: determining whether an area that an object contacts the opposed jaws is changing using the fiber strain, wherein the object is between the opposed jaws; (h) a change in the area that the object contacts the opposed jaws is indicative of the object moving relative to the opposed jaws; (i) the method further comprises: determining a degree of wear of the hinged tool by comparing the at least one of the tool strain applied to the hinged tool and the degree of pivoting of the hinged tool to a predetermined condition of the hinged tool; (j) the method further comprises adjusting control parameters for the hinged tool based on the degree of wear; (k) the method further comprises determining a remaining amount of useful life of the hinged tool based on the degree of wear; and/or (1) the method further comprises determining whether the tool is safe to use based on the degree of wear.

An aspect of the present technology includes a tool system comprising a hinged tool and a control system. The hinged tool comprises: a first member; a second member pivotally connected to the first member at a pivot; and a single core optical fiber fixed to the first member along a load application region such that fiber strain is induced in the single core optical fiber when tool strain is induced in the load application region. The control system is configured to: measure fiber strain in the optical fiber; and determine at least one of tool strain applied to the hinged tool and a degree of pivoting of the hinged tool using the fiber strain.

One or more aspect and examples above may be advantageous. For example, sensing the angle and distributed loading of robotically controlled surgical forceps can allow more precise application of forces to tissue, and reduce trauma to the tissue. Changes in the load profile of the forceps can determine if an object (such as a needle or tissue) is slipping within the forceps. Providing more precise information or other feedback (such as kinesthetic feedback, visual feedback, aural feedback, etc.) may allow less stiff and potentially tougher materials to be used in the construction of the forceps. Precise feedback may also allow a control system to compensate for changes in the mechanical properties of the instrument due to wear, thus extending the useful lifetime of the instrument. The precise measurement of loading and angle may also be used to determine the condition of the instrument, and how much useful life is left in the instrument and/or whether the instrument is safe to use.

Other aspects, features, and advantages of this technology will become apparent from the following detailed description when taken in conjunction with the accompanying drawings, which are a part of this disclosure and which illustrate, by way of example, principles of this technology.

DETAILED DESCRIPTION

The following description is provided in relation to several examples which may share common characteristics and features. It is to be understood that one or more features of any one example may be combinable with one or more features of the other examples. In addition, any single feature or combination of features in any of the examples may constitute additional examples.

As used herein, load is intended to encompass forces (e.g., point loads and distributed loads such as pressure or multiple point loads) acting externally on the tool. For example, if the forceps 100 grips tissue, the tissue will exert a load on the forceps. Strain as used herein should be interpreted as having its ordinary meaning but is typically discussed herein in relation to or as a result of the load applied to the tool or user actuated displacement of the tool. When optical fibers are bent due to an external load or by user commanded movement of the tool, strain will be induced in the optical fiber and that strain can be measured. The strain can then be correlated with load and/or displacement such as angular or linear displacement based on the known mechanical configuration of the tool (e.g., shape and/or material properties).

Figure 1:
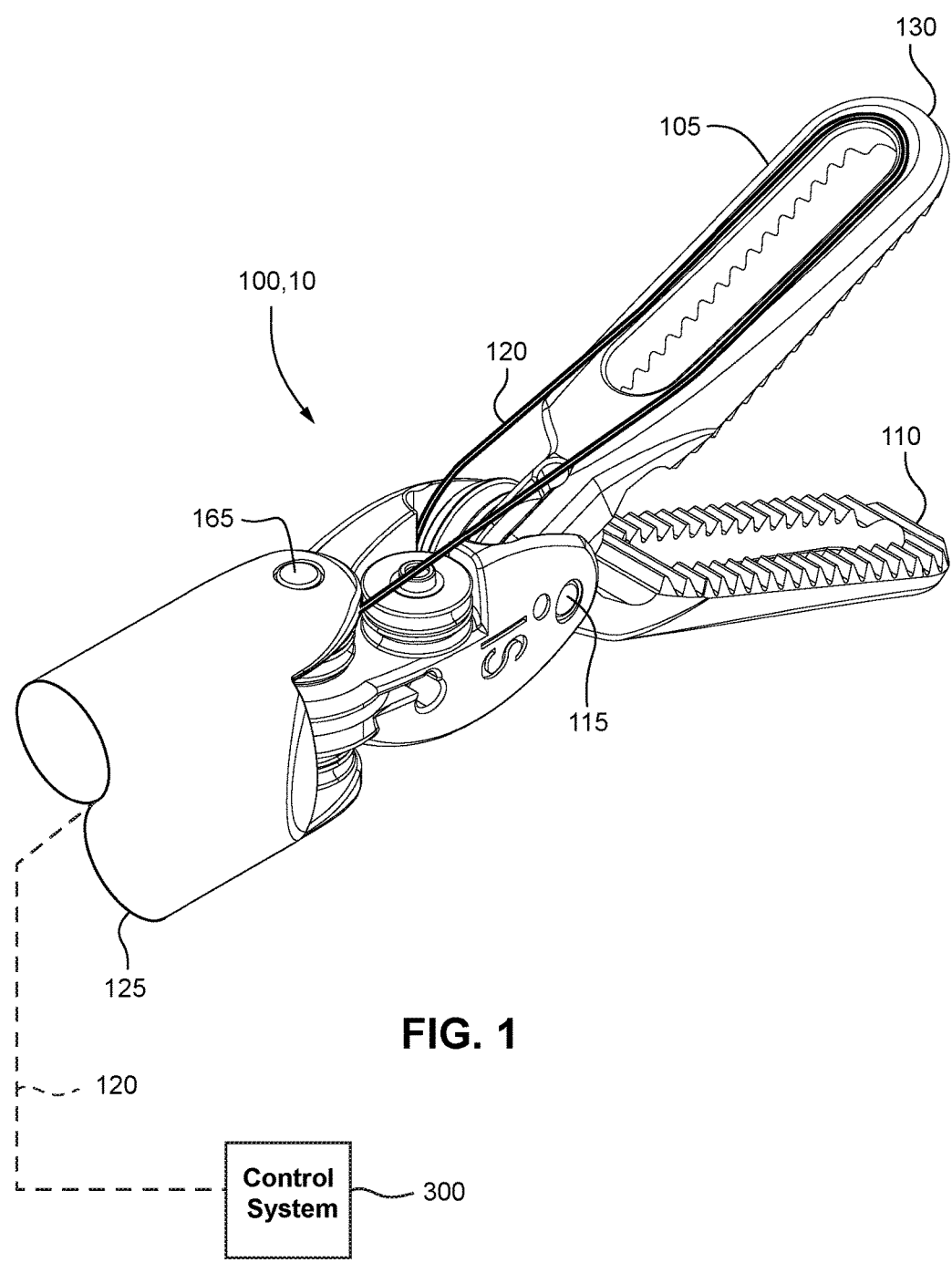
FIG. 1 is a first perspective view of forceps.
Figure 2:
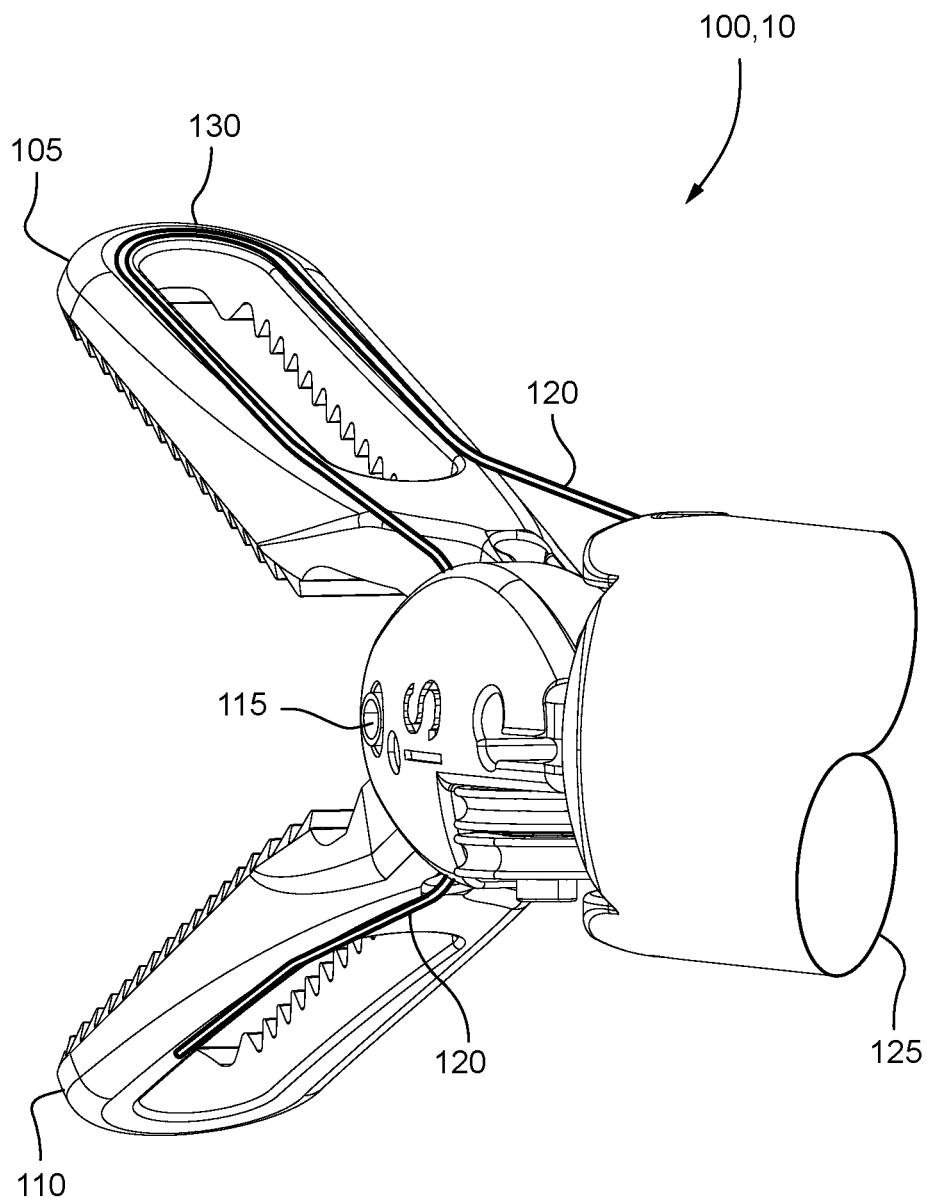
FIG. 2 is a second perspective view of the forceps.

FIGS. 1 and 2 illustrate the end of a forceps 100 (an example of a hinged tool 10) with a first jaw 105 (an example of a first member) and second jaw 110 (an example of a second member) that are movable relative to one another about a pivot (in this example, the pivot is centered about a simple pivot point 115). While the hinged tool 10 is shown as forceps 100 in this embodiment, it should be understood that the hinged tool 10 can include any tool with a first jaw 105, a second jaw 110 and a pivot point 115 including but not limited to scissors, clamps, forceps, graspers, retractors, clip appliers, dissectors, needle drivers, shears, stabilizers, cautery instruments, vessel sealers, or staplers. An optical fiber 120 (which may be a multi-core or single core optical fiber depending on the desired measurements) extends from a proximal end 125 (partially illustrated) and is attached to the first jaw 105 along a portion of the first jaw 105 where load is likely to be applied in use (an example of a load application region). The optical fiber 120 loops around a distal end 130 of the first jaw 105 (also a distal end of the forceps 100) and back towards the pivot point 115 (where it is occluded from view in these figures) and then to the second jaw 110 where it is attached to a portion of the second jaw 110 where load is likely to be applied in use (an example of a load application region). The optical fiber 120 is thus attached in a manner that causes the optical fiber 120 to flex, and undergo strain, when the first jaw 105 and the second jaw 110 move relative to one another. The optical fiber 120 will also flex, and undergo strain, when either the first jaw 105 or the second jaw 110 flex.

With this arrangement, the position of the jaws 105, 110 and an applied load on the jaws 105, 110 can be determined by way of the optical fiber 120. The relative angular position of the jaws can be determined by an amount that the optical fiber 120 bends between the jaws (i.e., adjacent the pivot point 115) and the load can be determined by strain in the optical fiber 120 along the jaws. Any strain imparted to the jaws by a load will result in a corresponding strain being induced in the optical fiber 120. As discussed in greater detail below, the distribution of the load can be used to determine where an object is clamped and/or what object is clamped. The amplitude of the strain distribution can be used to assess the stiffness of the material being clamped. This may be used to provide tactile or visual feedback to the user which may mimic or act as a surrogate for using the instrument by hand.

The shape of the optical fiber 120 along the jaws can also be used to determine wear of the forceps 100. For example, the initial shape of optical fiber 120 along the first jaw 105 and/or the second jaw 110 can be measured in a known state (e.g., closed) prior to a first use and then stored. After the forceps 100 is used, the same measurement can be made and compared to the stored value. If the change in shape exceeds an allowable limit, then the forceps 100 can be determined to have been damaged and/or used beyond their useful life and discarded or repaired. This could happen, for example, if the jaws bend or are worn over time and the angle between the jaws changes in the known state. Alternatively, wear may occur in an actuation mechanism. If wear occurs in the actuation mechanism, the movement of the jaws caused by the actuation mechanism may be compared to the ideal movement of the jaws based on how the back end of the tool is being actuated. Any deviation between actual and ideal may be used to determine remaining life or to compensate for a wearing tool.

Figure 3:
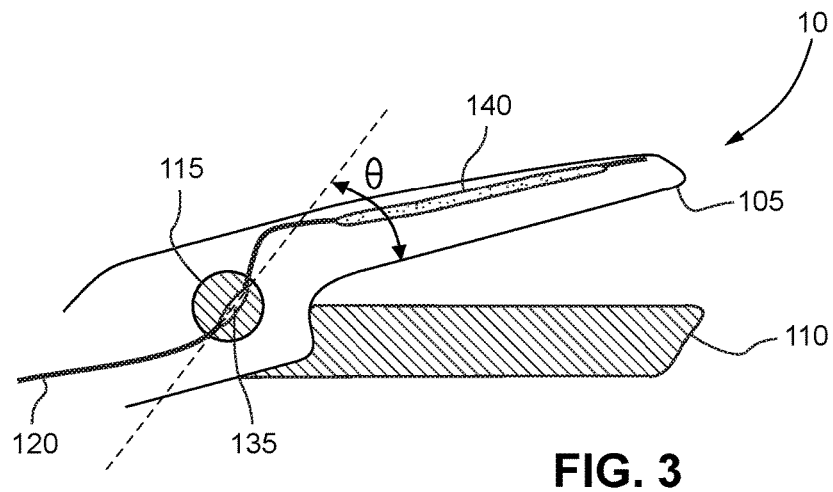
FIG. 3 is a partial view of a hinged tool.

FIG. 3 illustrates another implementation of an optical fiber 120 to sense the parameters of a hinged tool 10. Here the hinged tool 10 is illustrated in a simplified representation that could be scissors, a clamp, forceps, or any other tool with a first jaw 105, a second jaw 110 and a pivot point 115. Here, the second jaw 110 and the pivot point 115 are hatched to indicate that they are part of the same structure and/or connected in a manner so that they move in accordance with one another. Other similar figures are not hatched to simplify those figures but a similar structure where the second jaw 110 and the pivot point 115 move in accordance with one another should be understood. The optical fiber 120 is fixed to the pivot point 115 (here, illustrated as a pin-like structure) for a first length 135 and along the first jaw 105 for a second length 140 (an example of a load application region). With the optical fiber 120 fixed in this manner, a bend will occur between the first length 135 and second length 140 depending on the relative position of the first jaw 105 and the second jaw 110. This bend can be correlated to the angle θ which corresponds to the angle between the first jaw 105 and the second jaw 110. Through this measurement, the degree of opening or closing of the jaws can be determined.

So long as adequate strain relief (e.g., sufficient slack length) is provided in the optical fiber 120 between the first length 135 and the second length 140, the jaws should be able to move through their intended range of motion without damaging the optical fiber 120.

Although the ability to know the angle of the jaws is useful, the angle alone does not indicate force exerted by the jaws or a position along the jaws where an object is engaged. With distributed strain information, the force exerted by the jaws and the distribution of that force can be determined.

Figure 4A:
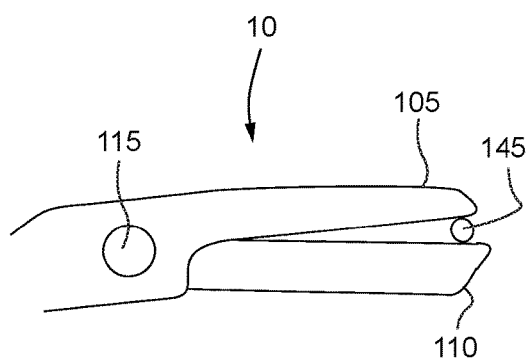
FIG. 4A is a partial view of a hinged tool with an object at a first position between jaws of the hinged tool.
Figure 4B:
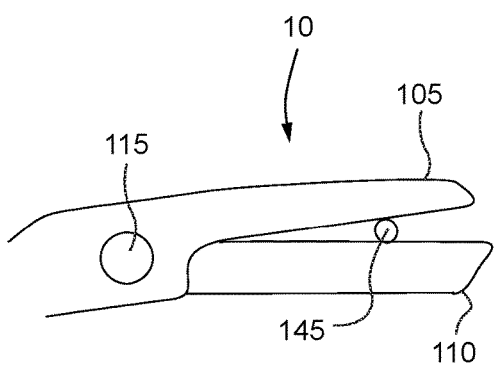
FIG. 4B is a partial view of a hinged tool with an object at a second position between jaws of the hinged tool.
Figure 4C:
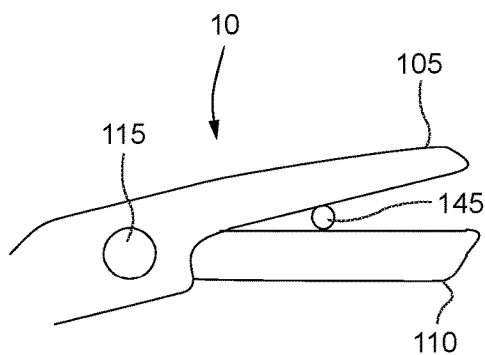
FIG. 4C is a partial view of a hinged tool with an object at a third position between jaws of the hinged tool.

The length 140 of the optical fiber 120 can be used to measure strain in the first jaw 105. Referring to FIGS. 4A-4D, an object 145 is illustrated at various positions progressing closer to the pivot point 115 in each successive figure. As can be appreciated, the strain distribution in the first jaw 105, and thus the optical fiber 120 along the second length 140, will vary depending on the location of the object 145. This strain distribution will be different from the clamped-closed condition illustrated in FIG. 5. Various exemplary measurement obtained with the optical fiber 120 in the configurations illustrated in FIGS. 4A-5 are illustrated in FIGS. 6, 7 and 9-11 as described below.

Figure 5:
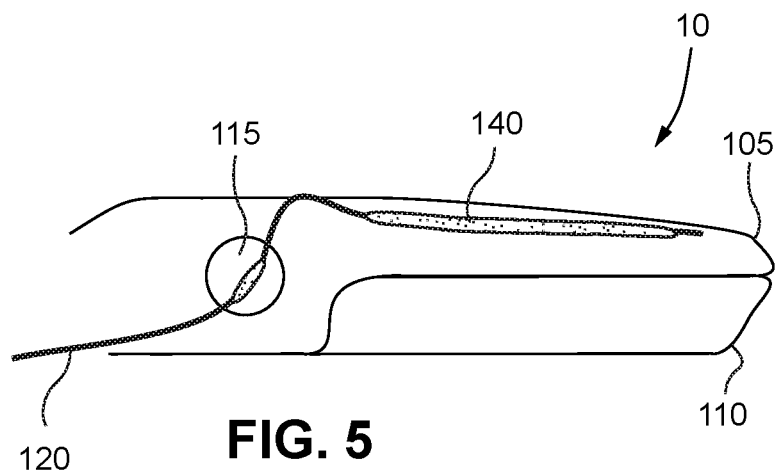
FIG. 5 is a partial view of a hinged tool with the jaws closed.
Figure 6:
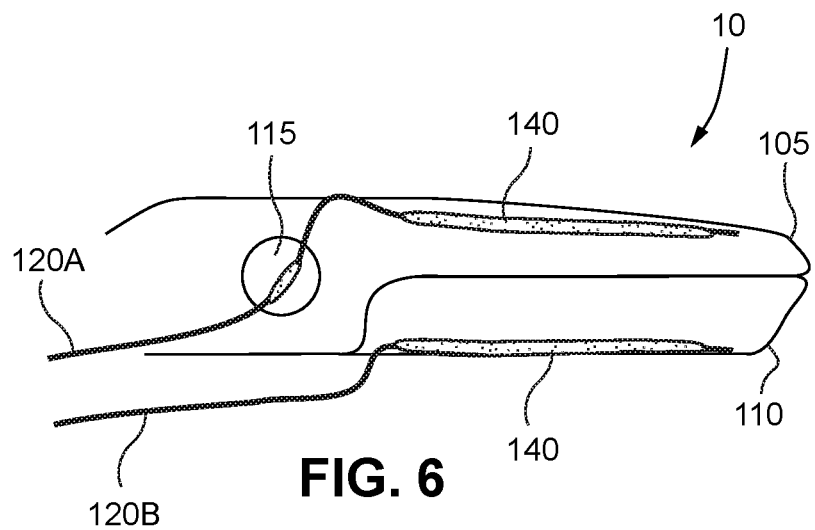
FIG. 6 is a partial view of a hinged tool with the jaws closed where separate fibers are illustrated on each jaw.

FIG. 6 illustrates a tool similar to FIG. 5 in that a tool 10 is illustrated with the jaws 105, 110 closed. But here two optical fibers 120A and 120B are illustrated on the first jaw 105 and the second jaw 110. This may allow calculations and measurement similar to the configuration illustrated in FIG. 1 where a single fiber is used for both jaws. Providing a separate fiber for each jaw may allow for redundancy and/or separate calculations or measurements for each jaw. Separate calculations or measurements for each jaw may be less complicated than with a single fiber for both jaws. However, adding fibers for each jaw may increase cost. Also, if the angular position of the jaws 105, 110 relative to one another is not relevant, the attachment at the pivot point may be omitted.

The optical fiber 120 may be a single core fiber or a multi-core fiber depending on the desired measurements and/or cost of the tool. For example, single core and multi-core fibers can both be used to measure strain and thus determine a load applied to a tool but a single core fiber should be less costly. Thus if only strain of the tool needs to be measured, a single core fiber is likely to be a more economical choice. If it is necessary or desirable to measure the angular orientation of the fiber (e.g., where and to what degree the fiber is bent), a multi-core fiber may be used. By including multiple cores that are twisted (e.g., helical), the strain in the cores will vary along the length of a bend. This variation in strain can be used to calculate the angle or shape of the fiber. The availability of both strain and angle may be useful. For example, with a multi-core fiber, the angle of the jaw could be mapped (because the angle of a fiber is measured) to the strain in the jaw (because the strain in the fiber is measured), which may be used to determine what is held in the jaws and/or where an object is held in the jaws.

Figure 4D:
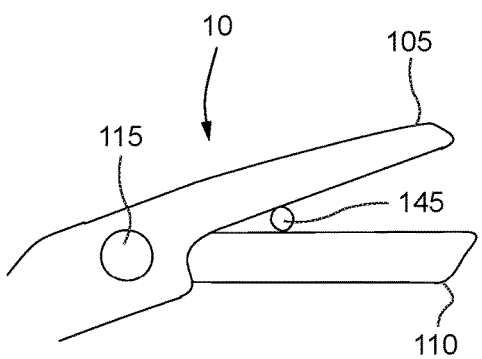
FIG. 4D is a partial view of a hinged tool with an object at a fourth position between jaws of the hinged tool.
Figure 7:
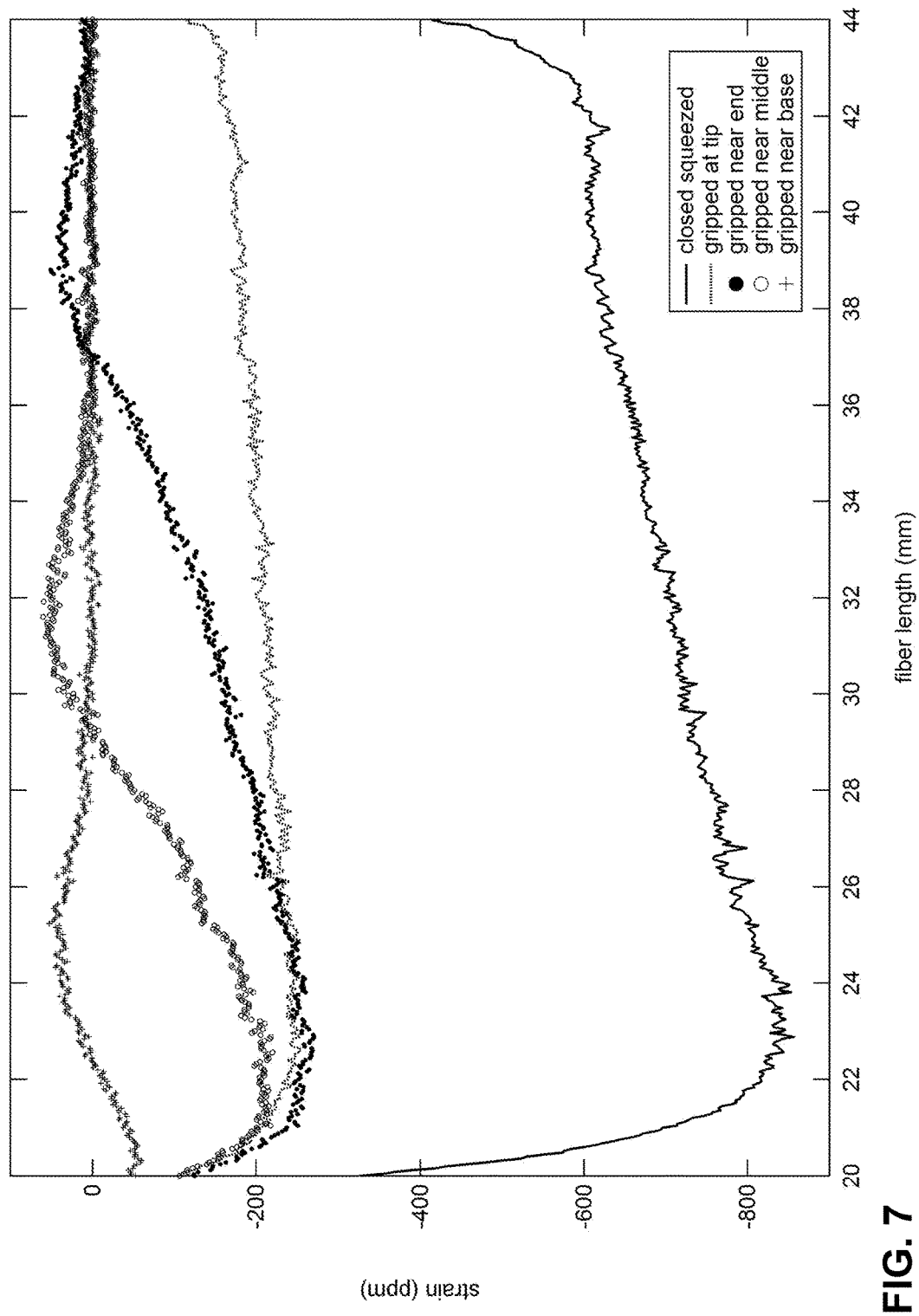
FIG. 7 is a graph of strain data corresponding to the hinged tool of FIGS. 4A-5.

FIG. 7 illustrates strain (in parts per million) versus fiber length in millimeters for the conditions illustrated in FIGS. 4A-5, which include closed squeezed (FIG. 5), gripped at tip (FIG. 4A), gripped near end (FIG. 4B), gripped near middle (FIG. 4C) and gripped near based (FIG. 4D). To gather the data in FIG. 7, the object 145 gripped in FIGS. 4A-4D was the shaft of a screwdriver, which is relatively hard (the optical fiber 120 is not illustrated in FIGS. 4A-4D). When this data was measured, the force applied in the closed condition was higher than the other cases which is exemplified by a higher strain level. The jaw design used to collect the data is configured such that when the jaws were closed with nothing between the jaws, the tips of the jaws contact one another first. This results in the closed strain profile being similar to the gripped at the tip strain profile. For any jaw configuration, the shape of the curves are likely to change based on factors such as shape of the object 145, hardness of the object 145, shape of the jaws, strength of the jaws, force applied, etc. All of these factors can be accounted for by gathering data with a given set of jaws and various objects that are likely to be encountered between the jaws.

Although the values of strain at any given point may be useful, the overall shape of the strain curve is indicative of the location where the object 145 is located within the jaws. In an application where the hinged tool 10 cannot be seen and/or visual information is limited, this can provide an indication of where the object 145 is. If this information is used in conjunction with a known location of the hinged tool 10 (which can be determined, for example, using shape sensing with the optical fiber 120), a user can determine if the correct object is between the jaws of the hinged tool 10. If the hinged tool 10 is a pair of scissors and is being used to cut or grab an object inside a mammalian body (e.g., needle, tissue or sutures), this type of strain measurement can be used to determine if the correct object is between the jaws and/or where it is between the jaws. And change in the distribution of strain can be used to determine if an object between the jaws is moving (e.g., slipping).

Figure 8:
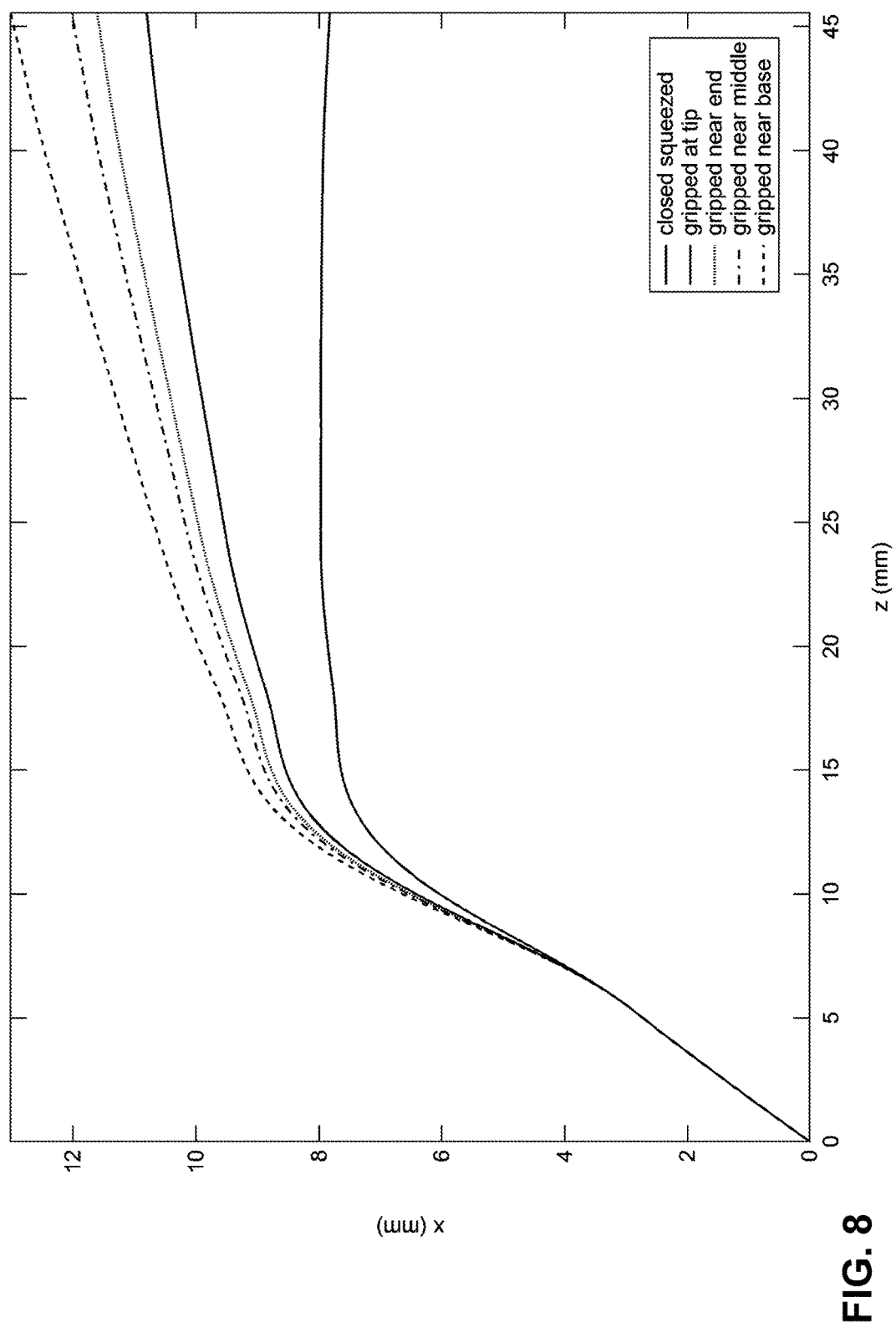
FIG. 8 is a graph of displacement data corresponding to the strain data of FIG. 7

FIG. 8 illustrates displacement data for the conditions illustrated in FIGS. 4A-5. The z-axis corresponds to a position on the first jaw 105 and the x-axis is displacement of the first jaw 105 at that position.

Figure 9:
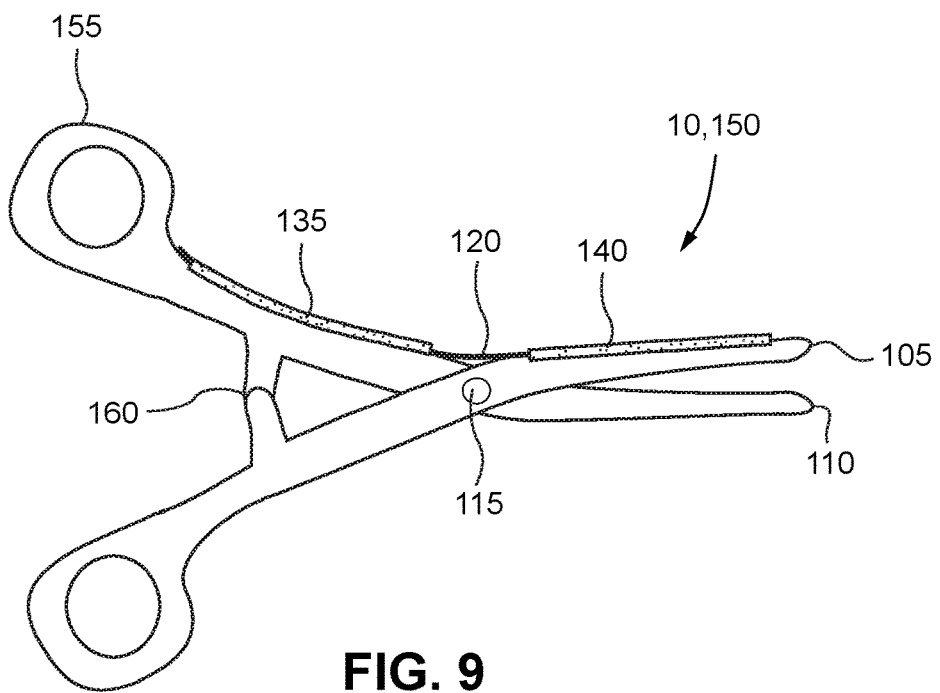
FIG. 9 is a view of another hinged tool.

FIG. 9 illustrates another hinged tool 10 in the form of a clamp 150 with an alternate configuration of the first length 135 and second length 140. Here, the first length 135 is between a grip 155 and the pivot point 115. Since the grip 155 is part of a continuous structure that includes the second jaw 110, the same data can be gather as where the first length 135 is attached to the pivot point 115 as described above. The clamp 150 includes a locking feature 160 that allows the clamp 150 to be maintained at various clamped positions. The locking feature 160 is similar to a series of successive snap fits (or "clicks") that result in discrete changes in distance.

Figure 10:
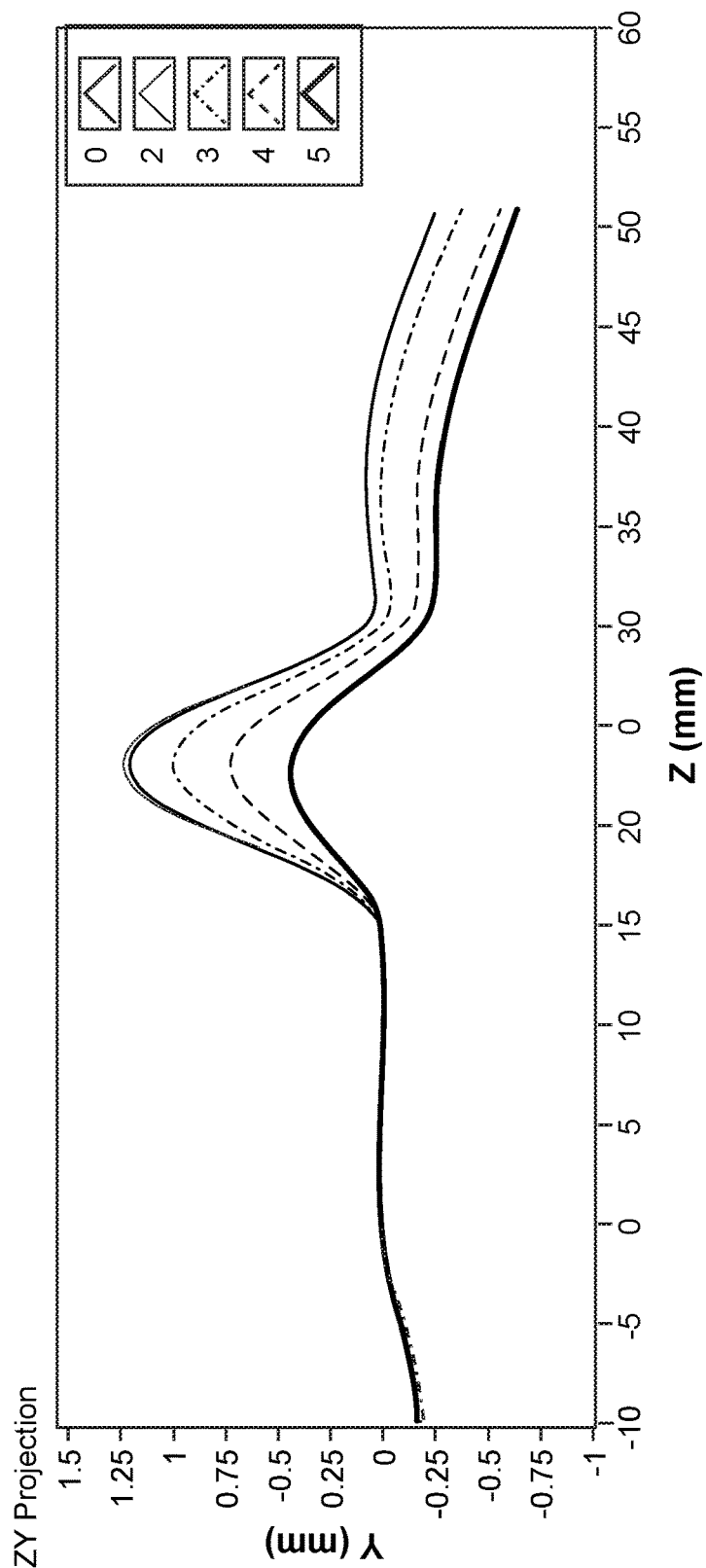
FIG. 10 is a graph of displacement data corresponding to the hinged tool of FIG. 9.
Figure 11:
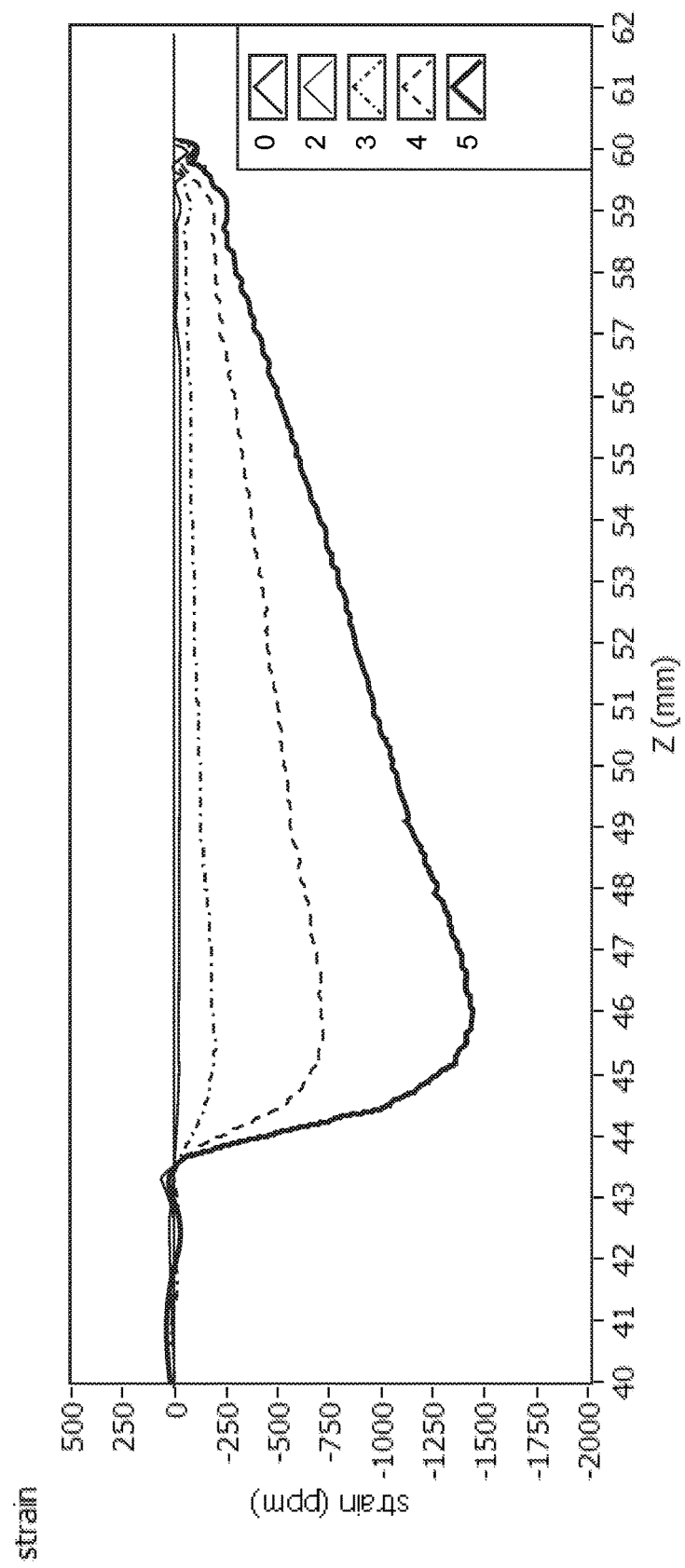
FIG. 11 is a graph of strain data corresponding to the hinged tool of FIG. 9.

FIG. 10 illustrates data collected using the configuration illustrated in FIG. 9. The numbers in the legend (0, 2 and 3-5) correspond to the number of clicks that the locking feature is engaged. For this data, a piece of rubber was gripped with the clamp 150. The total displacement is about half of a millimeter. The corresponding strain curves are illustrated in FIG. 11.

Figure 12:
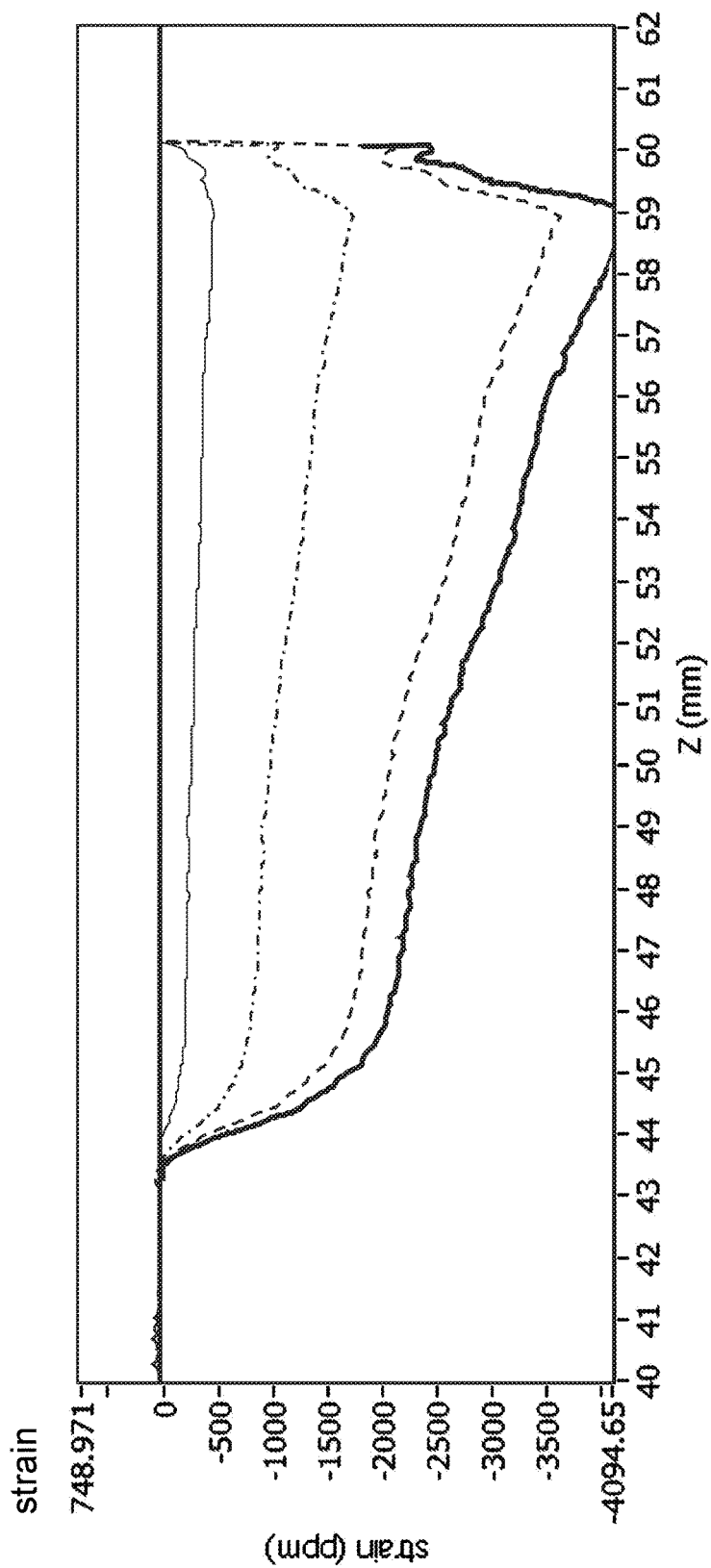
FIG. 12 is a graph of strain data corresponding to the hinged tool of FIG. 9.

FIG. 12 includes data collected using the clamp 150 but instead of clamping rubber, a toothpick was clamped. One significant aspect is that the shape of the curves in FIG. 12 differs from that in FIG. 10. Thus the strain profile can be indicative of an object between the jaws.

By collecting data for the hinged tool 10 and comparing it to prior data, control of the tool can be adjusted to account for tool wear. For example, if the collected data indicates that the jaws have been permanently deformed (e.g., bent or worn), the tool may still be useful if a correction factor is applied to control the angle of the jaws to account for the permanent deformation. The deformation or wear may be indicative of a remaining amount of useful life for the tool. Or if the deformation exceeds a predetermined amount, a warning can be issued indicating that the tool 10 is not safe for further use. These measurements could be accomplished with real time data or between uses as a calibration method.

Although the preceding description focused on tools with a single pivot point, any number of pivot points could be included. For example, with the forceps 100, not only can the present technology be applied to the pivot between jaws, but a second pivot 165 that allows the jaws to pivot together with respect to the proximal end 125 and normal to the pivot point 115. This angle could be measured if the proximal end of the fiber is in a constrained path in the proximal end 125 that allows for axial movement. Side to side motion that the joint allows (around the second pivot 165) may also be measured.

Also, the present technology can be applied to other types of pivots. The examples described herein generally include a pin at the pivot, such as the pivot associated with pivot point 115. However, the pivot could also be about a living hinge with a pivoting motion that is more complex than pure rotation about an axis through a single pivot point.

Figure 13:
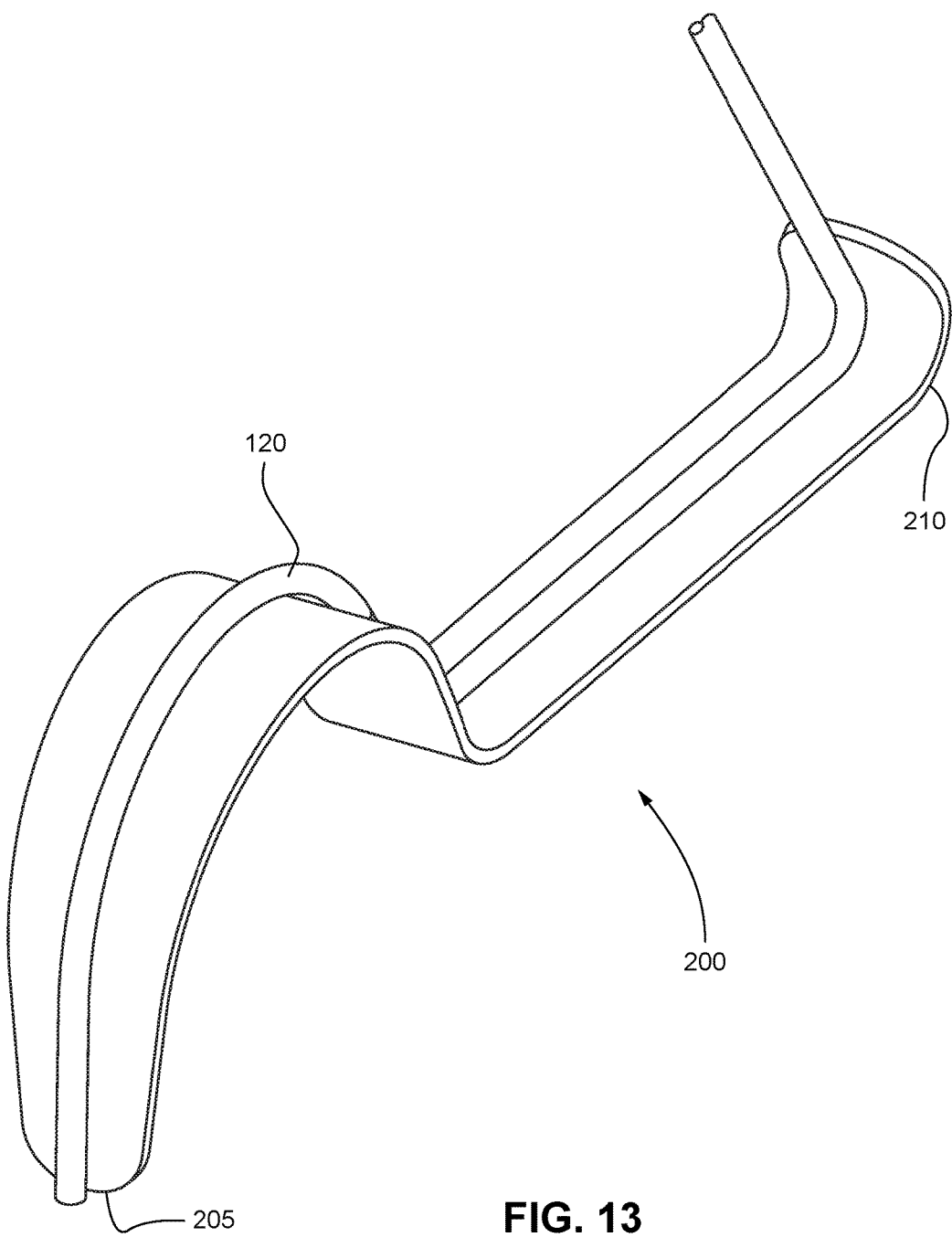
FIG. 13 is a perspective view of a non-hinged tool.

Alternatively, no pivot or hinge is required. FIG. 13 illustrates a tool 200 with an optical fiber 120, a distal end 205 and a proximal end 210. The proximal end 210 could be a grip suitable for grasping with a user's hand (as illustrated) or fixed to a robotic arm. The distal end 205 can be any suitable shape to interact with tissue. The tool 200 is illustrated as a surgical retractor, but the present technology may be applied to any tool that does not include a flexing or pivoting joint, hinge or pin as described in other examples. With this type of tool, any movement of one part of the tool with respect to another part of the tool would be by way of the material of the tool flexing. As with the tool 10, the strain measured in the optical fiber 120 may be correlated to the load applied by the tool 200. This may provide feedback to the user that may be useful, for example, in a remote-use situation.

The configuration of FIGS. 1 and 2 may also be advantageous because the strain data for the first jaw 105 and the second jaw 110 can be compared to make additional determinations. For example, if the strain is higher in one jaw than the other, this may be an indication that one of the jaws is caught or stuck and unable to properly engage the target. Similarly, if an object is clamped between the jaws and the strain in the jaws is substantially different, the difference in strain may indicate that the object between the jaws fixed to or caught on some other object. This may serve as an indication to change the orientation of the jaws and/or inspect the area of the jaws to determine if there is an issue, such as an obstruction, that should be remedied before completion of the procedure.

As is evident from the forgoing description, any instrument may include a shape sensor that detects anything that induces strain in the optical fiber 120. In some embodiments the tool can be a probe for palpation, retraction, etc. The probe can be rigid, flexible, jointed, hinged, or any other configuration that will allow the optical fiber 120 to gather information about the tissue effects and/or the tool. For example, the tool may be a probe similar to the tool 200. The tool may be similar to the tool 10 that includes an optical fiber 120 to provide information about the instrument itself. In other embodiments the optical fiber 120 could be incorporated into the instrument to allow the instrument to be used like the probe (e.g., integrate the optical fiber 120 into shears or forceps so that the jaws may be used for palpation), and in other embodiments the jawed instrument can be used to provide both instrument and tissue information using the same or different sets of optical fibers for the separate jaws.

The techniques described herein can be implemented using a control system 300 including at least one memory and at least one processor, and often a plurality of processors. The control system also includes programmed instructions (e.g., a computer-readable medium storing the instructions) to implement some or all of the methods described in accordance with aspects disclosed herein. The control system may include two or more data processing circuits with one portion of the processing optionally being performed on or adjacent the tool, and another portion of the processing being performed at a station (e.g. an operator input system or central processing system or the like) remote from the tool. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, the control system supports wireless communication protocols such as Bluetooth, IrDA, HomeRF, IEEE 802.11, DECT, and Wireless Telemetry. The control system may include a frequency domain reflectometer positioned in an operable relationship to an array of fiber Bragg gratings disposed within the optical fiber.

While the present technology has been described in connection with several practical examples, it is to be understood that the technology is not to be limited to the disclosed examples, but on the contrary, is intended to cover various modifications and equivalent arrangements included within the spirit and scope of the technology.

The invention claimed is:

1. A method of using a hinged tool, the method comprising:
    measuring fiber strain in an optical fiber fixed to at least one jaw of opposed jaws of the hinged tool; and
    determining at least one of tool strain applied to the hinged tool and a degree of pivoting of the hinged tool using the fiber strain.

2. The method according to claim 1, wherein determining the at least one of the tool strain applied to the hinged tool and the degree of pivoting of the hinged tool using the fiber strain comprises:
    determining both the tool strain applied to the hinged tool and the degree of pivoting of the hinged tool.

3. The method according to claim 1, wherein determining the at least one of the tool strain applied to the hinged tool and the degree of pivoting of the hinged tool using the fiber strain comprises determining the tool strain applied to the hinged tool, the method further comprising:
correlating the fiber strain to a force applied to the hinged tool.

4. The method according to claim 3, wherein correlating the fiber strain to the force applied to the hinged tool comprises:
correlating the fiber strain to a magnitude and a distribution of force applied to the hinged tool.

5. The method according to claim 1, further comprising: adjusting the hinged tool based on the at least one of the tool strain applied to the hinged tool and the degree of pivoting of the hinged tool.

6. The method according to claim 1, wherein determining the at least one of the tool strain applied to the hinged tool and the degree of pivoting of the hinged tool using the fiber strain comprises:
determining a distribution of the tool strain applied to the hinged tool along a predetermined length of the hinged tool.

7. The method according to claim 1, further comprising: determining a position where an object contacts the opposed jaws using the fiber strain, wherein the object is between the opposed jaws.

8. The method according to claim 1, further comprising: determining whether an area that an object contacts the opposed jaws is changing using the fiber strain, wherein the object is between the opposed jaws.

9. The method according to claim 1, further comprising: determining a degree of wear of the hinged tool by comparing the at least one of the tool strain applied to the hinged tool and the degree of pivoting of the hinged tool to a predetermined condition of the hinged tool.

10. The method according to claim 9, further comprising: adjusting control parameters for the hinged tool based on the degree of wear.

11. The method according to claim 9, further comprising determining at least one of a safety and a remaining amount of useful life of the hinged tool based on the degree of wear.

12. A tool system comprising:
a hinged tool comprising:
    a first member;
    a second member pivotally connected to the first member at a pivot such that the hinged tool has opposed jaws; and
    a single core optical fiber fixed to the first member along a load application region, wherein tool strain induced in the hinged tool in the load application region induces fiber strain in the single core optical fiber; and
a control system configured to:
    measure fiber strain in the optical fiber; and
    determine at least one of tool strain applied to the hinged tool and a degree of pivoting of the hinged tool using the fiber strain.

13. The tool system according to claim 12, wherein determining the at least one of the tool strain applied to the hinged tool and the degree of pivoting of the hinged tool using the fiber strain comprises:
determining both the tool strain applied to the hinged tool and the degree of pivoting of the hinged tool.

14. The tool system according to claim 12, wherein determining the at least one of the tool strain applied to the hinged tool and the degree of pivoting of the hinged tool using the fiber strain comprises determining the tool strain applied to the hinged tool, and further comprises:
correlating the fiber strain to a force applied to the hinged tool.

15. The tool system according to claim 12, wherein determining the at least one of the tool strain applied to the hinged tool and the degree of pivoting of the hinged tool using the fiber strain comprises:
determining a distribution of the tool strain applied to the hinged tool along a predetermined length of the hinged tool.

16. The tool system according to claim 12, wherein the control systems is configured to determine a position where an object contacts the opposed jaws using the fiber strain when the object is between the opposed jaws.

17. The tool system according to claim 12, wherein the control systems is configured to determine whether an area that an object contacts the opposed jaws is changing using the fiber strain when the object is between the opposed jaws.

18. The tool system according to claim 12, wherein the control systems is configured to determine a degree of wear of the hinged tool by comparing the at least one of the tool strain applied to the hinged tool and the degree of pivoting of the hinged tool to a predetermined condition of the hinged tool.

19. The tool system according to claim 18, wherein the control systems is configured to adjust control parameters for the hinged tool based on the degree of wear.

20. The tool system according to claim 18, wherein the control systems is configured to determine at least one of a safety and a remaining amount of useful life of the hinged tool based on the degree of wear.

* * * * *